(12) United States Patent
Fritz et al.

(10) Patent No.: US 7,843,563 B2
(45) Date of Patent: Nov. 30, 2010

(54) LIGHT SCATTERING AND IMAGING OPTICAL SYSTEM

(75) Inventors: Bernard S. Fritz, Eagan, MN (US); James A. Cox, New Brighton, MN (US); Peter Reutiman, Crystal, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/161,776

(22) Filed: Aug. 16, 2005

(65) Prior Publication Data

US 2007/0041013 A1    Feb. 22, 2007

(51) Int. Cl.
*G01N 15/02* (2006.01)
(52) U.S. Cl. ............... 356/336; 356/338; 356/73
(58) Field of Classification Search ......... 356/335–343, 356/39, 40, 73
See application file for complete search history.

(56) References Cited

U.S. PATENT DOCUMENTS

| | | | |
|---|---|---|---|
| 3,822,095 A | 7/1974 | Hirschfeld | |
| 3,871,769 A * | 3/1975 | Engel et al. | 356/336 |
| 3,928,094 A | 12/1975 | Angell | |
| 3,976,862 A | 8/1976 | Curbelo | |
| 4,273,443 A | 6/1981 | Hogg | |
| 4,284,412 A | 8/1981 | Hansen et al. | |
| 4,341,471 A * | 7/1982 | Hogg et al. | 356/343 |
| 4,478,076 A | 10/1984 | Bohrer | |
| 4,478,077 A | 10/1984 | Bohrer et al. | |
| 4,501,144 A | 2/1985 | Higashi et al. | |
| 4,599,000 A | 7/1986 | Yamada | |
| 4,651,564 A | 3/1987 | Johnson et al. | |
| 4,683,159 A | 7/1987 | Bohrer et al. | |
| 4,695,034 A | 9/1987 | Shimizu et al. | |
| 4,704,033 A | 11/1987 | Fay et al. | |
| 4,745,279 A | 5/1988 | Karkar et al. | |
| 4,818,263 A | 4/1989 | Mitch | |
| 4,874,949 A | 10/1989 | Harris et al. | |
| 4,911,616 A | 3/1990 | Laumann, Jr. | |
| 4,932,989 A | 6/1990 | Presby | |
| 5,017,497 A | 5/1991 | de Grooth et al. | |

(Continued)

FOREIGN PATENT DOCUMENTS

DE    10122321    4/2002

(Continued)

OTHER PUBLICATIONS

Altendorf et al, "Results Obtained Using A Prototype Microfluidics-Based Hematology Analyzer", SPIE Biomedical Optics 97, 1997.

(Continued)

*Primary Examiner*—Hoa Q Pham
(74) *Attorney, Agent, or Firm*—Crompton Seager & Tufte LLC

(57) ABSTRACT

An optical element for conveying scattered and image light to several detectors. The optical element may have the properties of a diffractive beam splitter and imaging lens. The detected light may be from an illuminated target. Further, there may be an optical element for conveying scattered light from a target via several zones to specific detectors, respectively. The latter optical element may include a multiple annular zone diffractive structure on a hybrid lens.

20 Claims, 4 Drawing Sheets

U.S. PATENT DOCUMENTS

| | | | |
|---|---|---|---|
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,171,132 A | 12/1992 | Miyazaki et al. | |
| 5,176,358 A | 1/1993 | Bonne et al. | |
| 5,185,641 A | 2/1993 | Igushi et al. | |
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,323,999 A | 6/1994 | Bonne et al. | |
| 5,416,580 A * | 5/1995 | Trainer | 356/336 |
| 5,428,443 A * | 6/1995 | Kitamura et al. | 356/336 |
| 5,441,597 A | 8/1995 | Bonne et al. | |
| 5,452,878 A | 9/1995 | Gravesen et al. | |
| 5,457,526 A | 10/1995 | Kosaka | |
| 5,510,267 A | 4/1996 | Marshall | |
| 5,528,045 A | 6/1996 | Hoffman et al. | |
| 5,570,193 A | 10/1996 | Landa et al. | |
| 5,601,080 A | 2/1997 | Oppenheimer | |
| 5,610,712 A | 3/1997 | Schmitz et al. | |
| 5,616,501 A | 4/1997 | Rodriguez et al. | |
| 5,633,724 A | 5/1997 | King et al. | |
| 5,683,159 A | 11/1997 | Johnson | |
| 5,716,852 A | 2/1998 | Yager et al. | |
| 5,717,631 A | 2/1998 | Carley et al. | |
| 5,726,751 A | 3/1998 | Altendorf et al. | |
| 5,757,476 A | 5/1998 | Nakamoto et al. | |
| 5,760,900 A | 6/1998 | Ito et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,839,807 A | 11/1998 | Perlo | |
| 5,863,502 A | 1/1999 | Southgate et al. | |
| 5,880,474 A | 3/1999 | Norton et al. | |
| 5,893,722 A | 4/1999 | Hibbs-Brenner et al. | |
| 5,901,939 A | 5/1999 | Cabuz et al. | |
| 5,922,210 A | 7/1999 | Brody et al. | |
| 5,932,100 A | 8/1999 | Yager et al. | |
| 5,948,684 A | 9/1999 | Weigl et al. | |
| 5,970,315 A | 10/1999 | Carley et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,054,335 A | 4/2000 | Sun et al. | |
| 6,061,131 A * | 5/2000 | Igushi et al. | 356/336 |
| 6,082,185 A | 7/2000 | Saaski | |
| 6,084,670 A * | 7/2000 | Yamazaki et al. | 356/343 |
| 6,091,197 A | 7/2000 | Sun et al. | |
| 6,091,537 A | 7/2000 | Sun et al. | |
| 6,094,293 A | 7/2000 | Yokoyama et al. | |
| 6,097,485 A | 8/2000 | Lievan | |
| 6,097,859 A | 8/2000 | Solgaard et al. | |
| 6,106,245 A | 8/2000 | Cabuz | |
| 6,109,889 A | 8/2000 | Zengerle et al. | |
| 6,116,756 A | 9/2000 | Peeters et al. | |
| 6,124,663 A | 9/2000 | Haake et al. | |
| 6,139,800 A | 10/2000 | Chandler | |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,236,458 B1 * | 5/2001 | Igushi et al. | 356/336 |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,262,845 B1 | 7/2001 | Sweatt | |
| 6,281,975 B1 | 8/2001 | Munk | |
| 6,382,228 B1 | 5/2002 | Cabuz et al. | |
| 6,462,869 B1 | 10/2002 | Gutjahr | |
| 6,493,155 B1 * | 12/2002 | Lee et al. | 359/742 |
| 6,549,275 B1 | 4/2003 | Cabuz et al. | |
| 6,597,438 B1 | 7/2003 | Cabuz et al. | |
| 6,678,429 B2 | 1/2004 | Mossberg et al. | |
| 6,700,130 B2 * | 3/2004 | Fritz | 250/573 |
| 6,760,107 B1 | 7/2004 | Drake | |
| 6,850,324 B1 * | 2/2005 | De Metz | 356/336 |
| 6,859,276 B2 * | 2/2005 | Xu | 356/336 |
| 6,946,620 B2 * | 9/2005 | Amako et al. | 219/121.75 |
| 7,002,684 B2 * | 2/2006 | Ikeda et al. | 356/336 |
| 2003/0142291 A1 | 7/2003 | Padmanabhan et al. | |
| 2005/0083524 A1 * | 4/2005 | Totoki | 356/336 |
| 2005/0122522 A1 | 6/2005 | Padmanabhan et al. | |
| 2005/0151968 A1 | 7/2005 | Drake et al. | |
| 2008/0221711 A1 * | 9/2008 | Trainer | 700/54 |

FOREIGN PATENT DOCUMENTS

| | | |
|---|---|---|
| EP | 0269076 | 6/1988 |
| EP | 1001326 | 5/1999 |
| EP | 1134548 | 9/2001 |
| EP | 1396736 | 3/2004 |
| JP | 61066947 | 4/1986 |
| JP | 08128941 | 5/1996 |
| JP | 10073528 | 8/1996 |
| JP | 2000056228 | 7/1999 |
| WO | WO 95/27199 | 3/1995 |
| WO | WO 99/60397 | 4/1999 |
| WO | WO 01/09598 | 2/2001 |
| WO | WO 02/10713 | 2/2002 |
| WO | WO 02/10714 | 2/2002 |

OTHER PUBLICATIONS

Altendorf et al., "Differential Blood Cell Counts Obtained Using A Microchannel Based Flow Cytometer", Solid State Sensors & Actuators, vol. 1, 531, 1997.

Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.

Altendorf et al., "Microfabrication Technology For Research And Diagnostics, Silicon Microchannel Optical Flow Cytometry", SPIE Proceedings, Biomedical Optics 96, Jan. 1996.

Cabuz et al., "Mesoscopic Sampler Based on 3D Array of Electrostatically Activated Diaphragms"; The 10th Int. Conf. On Solid-State Sensors and Actuators, Transducers'99, Jun. 7-12, 1999, Sendai Japan, p. 1890-1.

Darling et al., "Integration Of Microelectrodes With Etched Microchannels For In-Stream Electrochemical Analysis", MicroTAS 98, Banff, Canada, Apr. 1998.

Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.

Hatch et al., "Microfluidic Approaches To Immunoassays", SPIE conference on Micromachining and Microfabrication Symposium at Santa Clara, CA, Sep. 20-22, 1999.

http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

http://www.micronics.net/tsensor.htm, pp. 1-4, downloaded Jun. 14, 2000.

http://www.xmission.com/~ralcon/phasemat.html, Rallison, "Phase Materials for HOE Applications," 13 pages, printed Apr. 1, 2005.

Huang et al., "Development Of A Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3$^{rd}$ International Conference on Micro Opto Electro Mechanical Systems (MOEMS 99), Aug. 30-Sep. 1, 1999, Mainz, Germany, pp. 165-170.

Toshiyoshi et al., "Surface micromachined 2D Lens Scanner Array", Proc. IEEE?LEOS International Coference on Optical EMMS/Sheraton Kauai Resort, Kauai, Hawaii, Aug. 21-24, 2000, 2 pages.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantranont et al., "MEMS-Controllable Microlens Array For Beam Steering and Precision Alignment in Optical Interconnect Systems", Solid-State Sensor and Actuator Workshop, Hilton Head Island, South Carolina, Jun. 4-8, 2000, pp. 101-104.

Weigh et al, "Silicon-Microfabricated Diffusion-Based Optical Chemical Sensor", Reprint from "Sensors & Actuators" B 38-39, 452-457, 1997.

Weigl et al, "Microfluidic Diffusion-Based Separation And Detection", Science, vol. 283, pp. 346-347, Jan. 15, 1999.

Weigl et al, "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II—SPIE vol. 3606, Jan. 25-26, 1999.

Weigl et al, "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection In Silicon Flow Structures", B. Weigl et al., Analytical Methods & Instrumentation, µTTAS 96 special edition, 1996.

Weigl et al., "Fluorescence And Absorbance Analyte Sensing In Whole Blood And Plasma Based On Diffusion Separation In Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads", µTTAS 96 Conference Proceedings, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Yager et al., "Applying Microfluidic Chemical Analytical Systems To Imperfect Samples", Micro Total Analysis Systems 98, D. Harrison & A. van den Berg (ed.), Kluwer Academic Publishers, Dordrecht, 207-212, 1998.

Yager et al., "Design Of Microfluidic Sample Preconditioning Systems For Detection Of Biological Agents In Environmental Samples", Yager, M. et al., SPIE Proceedings, 3515, 252-259, 1998.

Cox, "Replicated Hybrid Optics for Display Applications," SID Digest, pp. 183-186, Jun. 14, 1994.

* cited by examiner

LIGHT SCATTERING AND IMAGING OPTICAL SYSTEM

BACKGROUND

The invention pertains to optical arrangements, and particularly to those involving scattered light. More particularly, the invention pertains to collecting information from scattered light and images.

SUMMARY

The invention is an optical system for obtaining data from a region of interest with imaging and scattering detection and measurements of light.

DESCRIPTION

Figure 1:
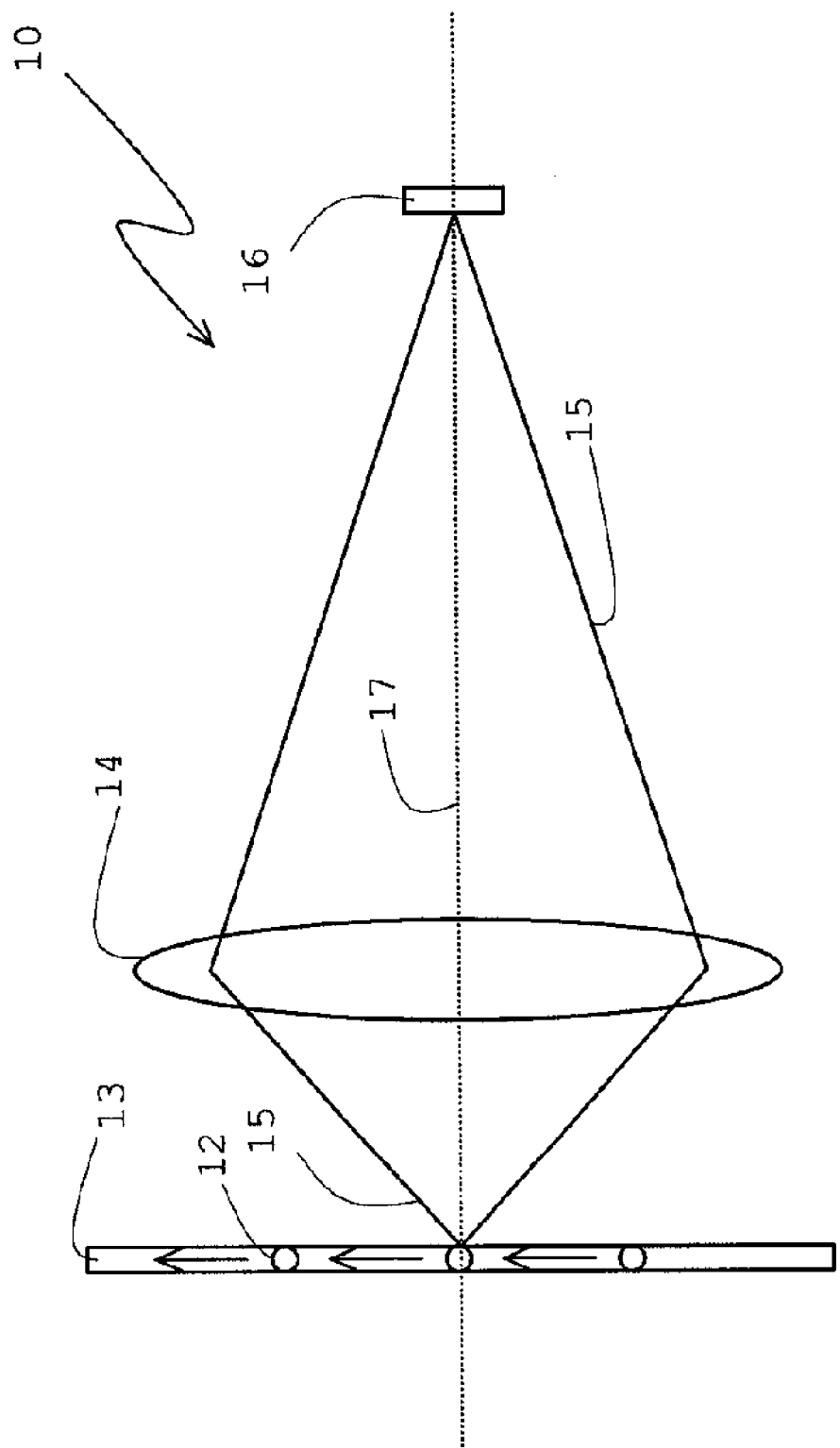
FIG. 1 is an optical imaging channel for determining particle diameter and flow rate.
Figure 2:
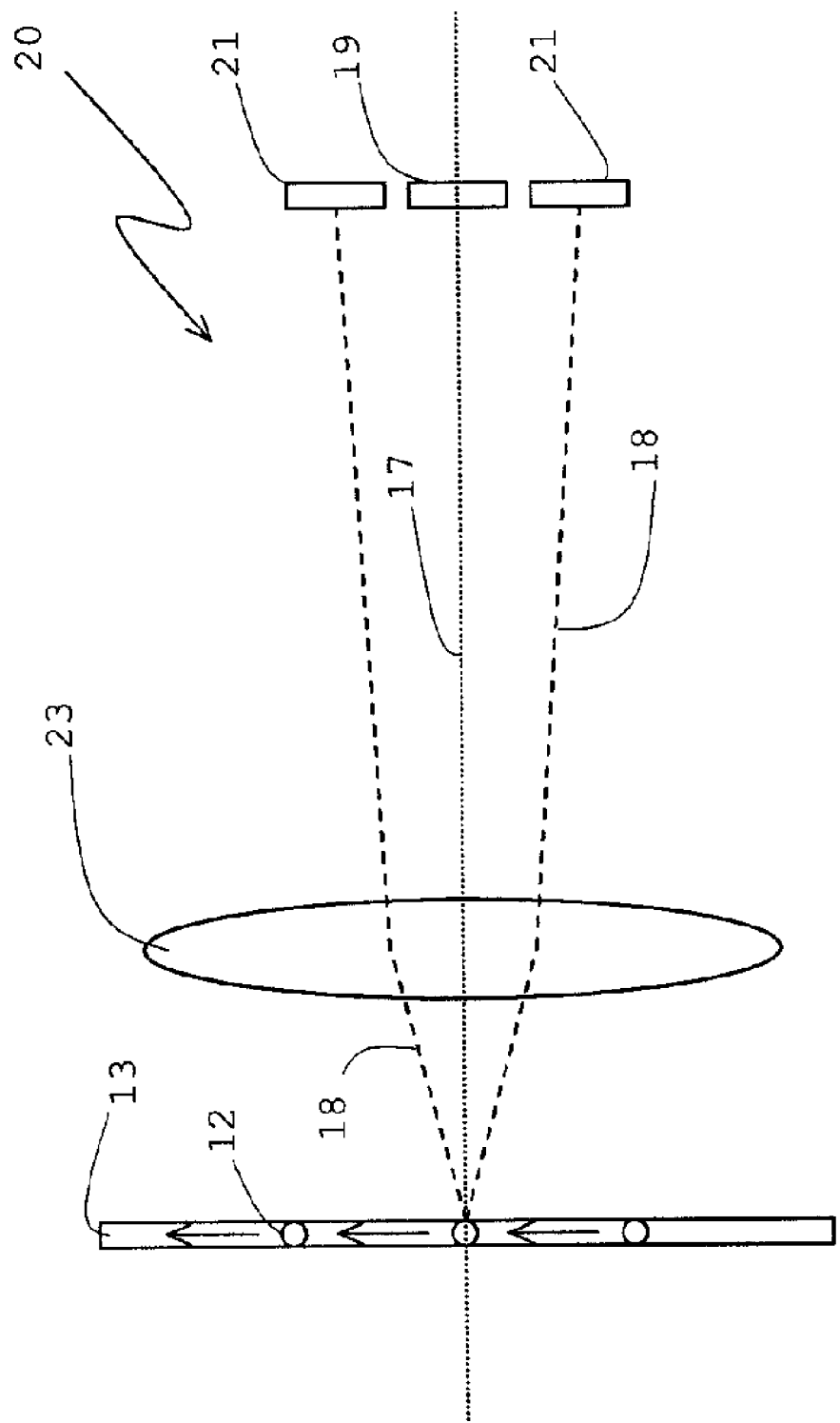
FIG. 2 is an optical scattering channel for determining particle type.
Figure 3:
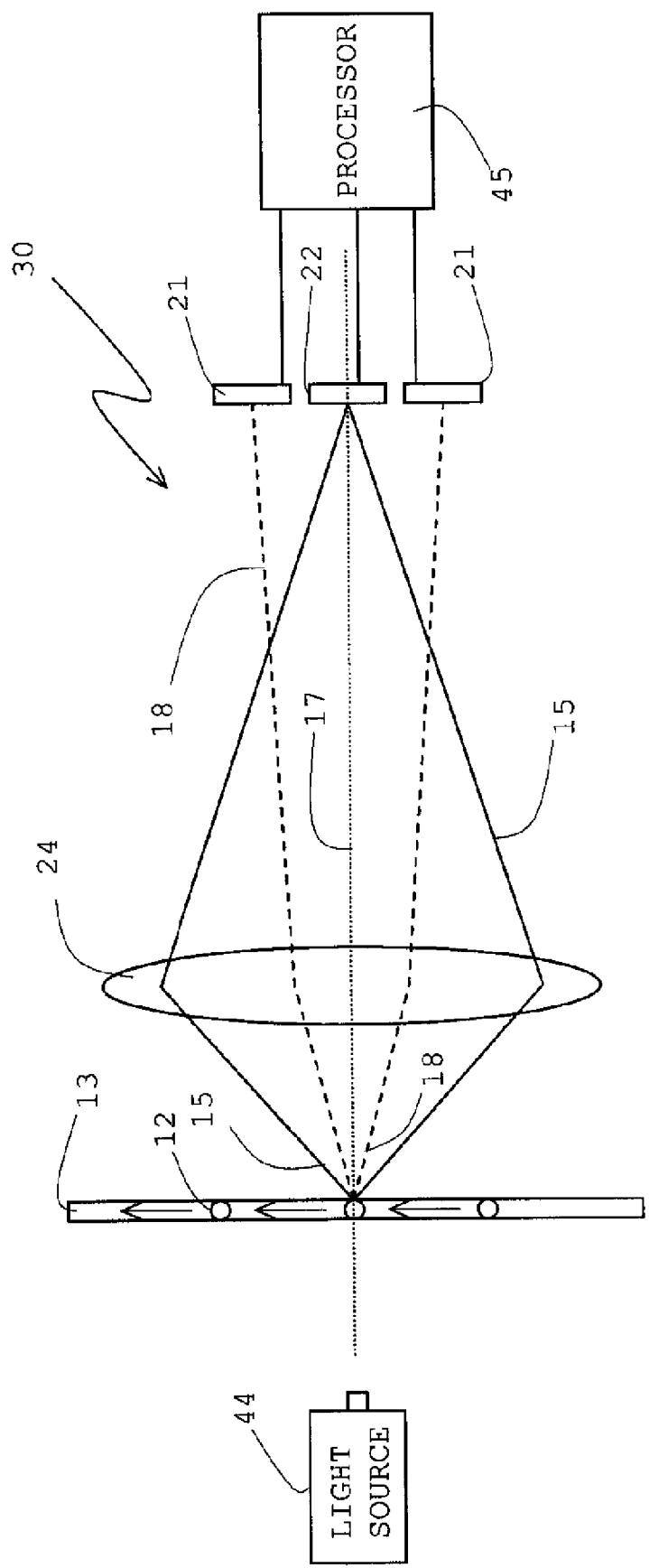
FIG. 3 is a combination optical imaging and scattering channel.

There may be system that collects both scattering and imaging information of an event such as in a cytometer flow channel and that of a cell, for example, a white or red blood cell. For instance, in cytometery, some of the goals may include a classification and counting of cell types along with a measurement of cell volume. An all optical approach to these goals may be achieved by measuring light scattered off of a cell at various angles along with imaging the cell to determine its diameter, and possibly other properties. The imaging and scattering may be accomplished with two independent optical systems, as illustrated in FIGS. 1 and 2, respectively. However, with the present approach, the scattering and imaging may be accomplished with one independent optical system, as illustrated in FIG. 3. The use of a diffractive or hybrid (i.e., diffractive-refractive) optical element may permit one to achieve an optical train that accomplishes both imaging and scattering.

FIG. 1 illustrates an optical imaging channel or train 10 that may be used for determining a diameter and flow rate, for example, of blood cells 12 (or other particles) in a flow channel 13. An imaging lens 14 may focus light 15 from a cell 12 on an imaging detector 16. Detector 16 may be an array of photodetectors or some other mechanism for image detection. Lens 14 and detector 16 may be aligned along an optical axis 17.

FIG. 2 illustrates an optical scattering channel or train 20 that may used for determining a type, and/or other property, of blood cell 12 (or other particle) in a flow channel 13. Light 18 scattered off of cell 12 may go through a lens 23 which may operate as a scatter collection lens. Scattered light 18 may be redirected by lens 23 which may proceed on to a detector 21. Detector 21 may be a photodetector or an array of photodetectors or some other mechanism. Detector 21 may be an annular-shaped detector. Detector 21 may detect FALS (forward angle scattering) and/or SALS (small angle scattering) of light. Detector 19 may be an extinction channel (unscattered by cell 12) for light that may be proceeding along optical axis 17.

FIG. 3 is a combination scattering and imaging channel or train 30 that may be used for determining a diameter, flow rate and/or type (and/or including possibly other properties) of blood cells 12 (or other particles 12) in the flow channel 13, or items in a region of interest. The particles 12 may be illuminated by a light source 44. Lens 24 may focus light 15 from a cell 12 on an imaging detector 22 with a double slit. Lens 24 may be regarded as a diffractive beam splitter channel. Light 15 may be of a plus first order imaging. Detector 22 may consist of an array of photodetectors or some other mechanism for image detection and as a scattering extinction channel. Lens 24 may collect scattered light 18 of a minus first diffracted order which may proceed on to detector 21. Detector 21 may be a photodetector or an array of photodetectors or some other mechanism. Detector 21 may be an annular-shaped detector. Detector 21 may detect FALS and/or SALS light. Detector 22 may be part of an extinction channel for light that may proceed along optical axis 17. Detectors 16, 19, 21 and 22 may also be regarded as a part of an imaging channel, an extinction channel, a FALS/SALS scattering channel and/or an imaging channel with a double slit, respectively. Signals from the detectors 21 and 22 may go to a processor 45 for analysis of signals and outputs of information about the target 12.

Figure 4:
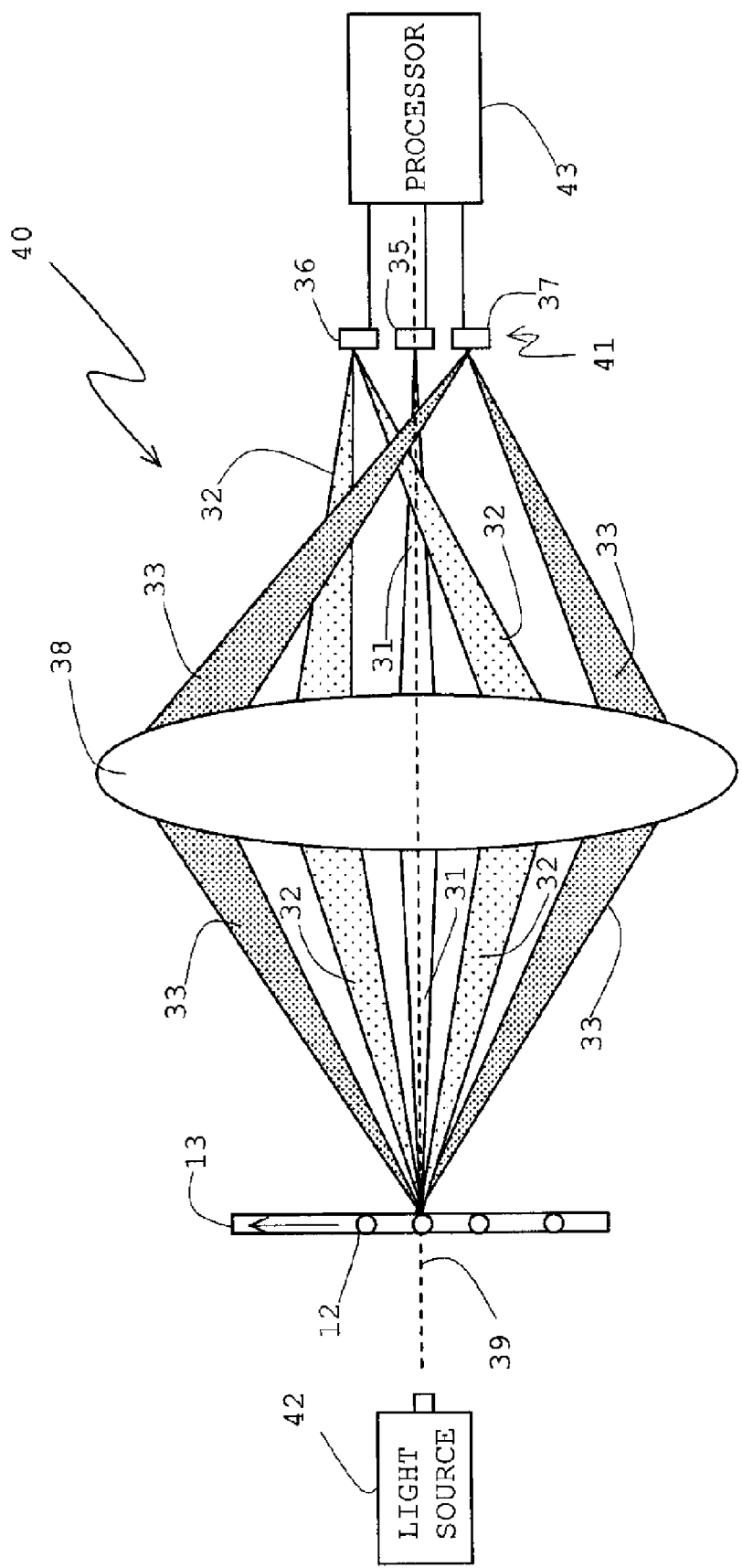
FIG. 4 is an optical scattering device having a multiple zone diffractive structure.

An angular scatter collection channel 40 (FIG. 4) may be implemented to collect efficiently and compactly angular zones 31, 32 and 33 of scattered light from a region of interest such as a flow channel 13 having cells 12 (or other particles) flowing in the channel. The region of interest or target may be illuminated by a light source 42. The flow channel 13 may be a part of a cytometer. Collected light may be redirected onto small detectors 35, 36 and 37 that are of similar area and close together. With a three angular zone diffractive surface structure on a hybrid lens 38, one may be able to collect annular zones 31, 32 and 33 of scattered light from the region of interest, and focus these different zones onto adjacent detectors 35, 36 and 37, respectively. By using the singular optical element 38 which combines both focusing and grating properties, a complete or nearly complete annular scattered region 31, 32, 33 may be captured and redirected onto a linear (or other configuration) detector array 35, 36, 37 in a compact module.

Each angular zone 31, 32 and 33, of the diffractive surface structure of optical element 38 may have an associated linear term (grating) that redirects captured scattered light over the respective region to a lateral position near an optical axis 39 of lens 38. Lens 38 may also serve to focus the captured scattered light. Each capture zone may be redirected by the diffractive structure on lens 38 in that particular zone to a different lateral position in a detector array plane 41 that may support, for instance, detectors 35, 36 and 37. The detectors may be of equal area, close together and/or compact with a maximum energy capture. Signals from detectors 35, 36 and 37 may go to a processor 43 for analyses of the signals, and an output of information about the targets 12. The light collection regions may include an extinction zone 31, a size zone 32 and a structure zone 33 which have scattered light directed to detectors 35, 36 and 37, respectively. Zone 33 may be the outermost zone from axis 39, as conveyed by the diffractive structure on lens 38. Zone 31 may be the intermost zone relative to axis 39, and zone 32 may be the intermediate zone between zones 31 and 33 relative to axis 39 of lens 38. There may instead be more or less than three zones in the angular scatter collection channel 40.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A system for scattered light capture, comprising:
a flow channel for conveying particles;
a light source for providing light through the flow channel;
a detector array for detecting light from the flow channel; and
a lens, situated between the flow channel and the detector array, having a plurality of annular zones and an axis, wherein each of the plurality of annular zones extends outward from the axis of the lens, wherein the lens is a hybrid lens having focusing and grating properties for affecting the light from the flow channel to the detector array; wherein at least one detector of the detector array is for detecting FALS and/or SALS scattered light and at least one detector of the detector array receives light of an image of the target.

2. The system of claim 1, wherein the plurality of annular zones includes at least an innermost zone, an intermediate zone, and an outermost zone with respect to the axis.

3. The system of claim 1, wherein a diffractive structure is on the lens.

4. The system of claim 1, wherein the plurality of annular zones comprises an extinction zone, a size zone and a structure zone.

5. The system of claim 4, wherein:
the extinction zone is projected on a first detector of the detector array;
the size zone is projected on a second detector of the detector array; and
the structure zone is projected on a third detector of the detector array.

6. The system of claim 4, wherein the plurality of annular zones conveys light scattered by a target.

7. A method for detection comprising:
providing a single optical element having a focusing lens with a diffracting structure having a plurality of angular diffractive zones;
providing a single detector array;
directing scattered light with the optical element from a target to a first detector of the detector array;
directing imaging light with the optical element from the target to a second detector of the detector array.

8. The method of claim 7, wherein the diffracting structure redirects captured scattered light in annular zones with respect to an axis of the lens onto adjacent detectors.

9. A method for detection comprising:
providing light through a flow channel for conveying particles;
providing a single optical element having both focusing and grating properties; and
directing both focused and scattered light from the flow channel with the optical element via a plurality of annular zones to a plurality of adjacent detectors on a single detector array, respectively; and the optical element comprises a multiple zone diffractive structure on a single lens.

10. The method of claim 9, wherein the plurality of annular zones comprises:
a first annular zone about an optical axis;
a second annular zone outside of the first annular zone; and
a third annular zone outside the second annular zone.

11. The method of claim 10, wherein said directing step includes:
directing scattered light via the first annular zone to a first detector of the plurality of detectors;
directing scattered light via the second annular zone to a second detector of the plurality of detectors; and
directing scattered light via the third annular zone to a third detector of the plurality of detectors.

12. The method of claim 11, wherein:
the first annular zone is an extinction zone;
the second annular zone is a size zone; and
the third annular zone is a structure zone.

13. The method of claim 11, wherein the flow channel is of a cytometer.

14. An optical system comprising:
a light source situated on an optical axis for illuminating particles in a flow channel which scatter light at the optical axis in the flow channel;
a single optical element, having an imaging lens with a plurality of angular zone diffractive surface structures, for focusing and redirecting scattered light from the particles on to an array of photodetectors, the array being approximately centered on the optical axis;
light scattered at a first angular zone relative to the optical axis is redirected by a diffractive surface structure of the optical element to a first detector of the array of photodetectors;
light scattered at a second angular zone relative to the optical axis is redirected by a diffractive surface structure of the optical element to a second detector of the array of photodetectors; and
light scattered at a third angular zone relative to the optical axis is redirected by a diffractive surface structure of the optical element to a third detector of the array of photodetectors; at least one detector of the array of photodetectors received light focused from the single optical element; wherein the light source illuminates the particles in the flow channel without intervening optical elements.

15. The system of claim 14, wherein:
the array of photodetectors is for detecting FALS and/or SALS scattered light.

16. The system of claim 14, wherein the first detector of the array of photodetectors is for a first diffractive order.

17. The system of claim 16, wherein the second detector of the array of photodetectors is for a second diffractive order.

18. The system of claim 17, wherein:
the array of photodetectors receives light of an image of the target.

19. The system of claim 18, further comprising a processor connected to the array of photodetectors.

20. The system of claim 14, wherein the flow channel is of a cytometer.

* * * * *